United States Patent [19]
Bab et al.

[11] Patent Number: 5,814,610
[45] Date of Patent: Sep. 29, 1998

[54] OSTEOGENIC GROWTH OLIGOPEPTIDES AND PHARMACEUTICAL COMPOSITIONS CONTAINING THEM

[75] Inventors: Itai Bab, M.P. Ayalon; Andras Muhlrad; Michael Chorev, both of Jerusalem; Arie Shteyer, Mevasseret Zion; Zvi Greenberg, Givat Zeev; Nura Mansur, TelAviv-Jaffa, all of Israel

[73] Assignee: Yissum Research Development Company of the Hebrew University of Jerusalem, Israel

[21] Appl. No.: 530,277

[22] PCT Filed: Mar. 4, 1994

[86] PCT No.: PCT/GB94/00416

§ 371 Date: Jan. 5, 1996

§ 102(e) Date: Jan. 5, 1996

[87] PCT Pub. No.: WO94/20529

PCT Pub. Date: Sep. 15, 1994

[30] Foreign Application Priority Data

Mar. 4, 1993 [IL] Israel ........................................ 104954

[51] Int. Cl.$^6$ .......................... A61K 35/18; A61K 37/36; C07K 15/06; C07K 7/08
[52] U.S. Cl. ................................ 514/17; 514/18; 530/330
[58] Field of Search .......................... 514/17, 18; 530/330

[56] References Cited

U.S. PATENT DOCUMENTS

| 4,434,094 | 2/1984 | Seyedin et al. ...................... 260/112 R |
| 4,455,256 | 6/1984 | Urist .................................... 260/112 R |

FOREIGN PATENT DOCUMENTS 0 241 578  10/1987  European Pat. Off. .
0 349 048   1/1990  European Pat. Off. .
0 572 122 A2  12/1993  European Pat. Off. .

OTHER PUBLICATIONS

Kharchenko, E. P.; Bagrov, A. Historphin—new opiate peptide from histone H4AU. Dokl. Akad. Nauk SSSR 289:1009–1012, 1986.

Viscontini et al. Pterin Chemistry . . . Helv. Chim Acta, 53(2), 377–383, 1970.

Bab et al (192): EMBO J. vol. 11, No. 5, pp. 1867–1873 Histone H4–related osteogenic growth etc.

Greenberg et al (1993) Biochim. Biophys Act. vol. 1178, No. 3 pp. 273–280 Mitogenic action of osteogenic etc.

Urist et al (1987) Meth. Enzymol. vol. 146 pp. 294–312 Preparation and Bioassay of Bone Morphogenetic etc.

Chemical Abstracts vol. 74, No. 1 Jan. 1971 Sautiere et al.

Chemical Abstracts vol. 76, No. 7 Feb. 1972 Sautiere et al.

*Primary Examiner*—Cecilia J. Tsang
*Assistant Examiner*—Michael Borin
*Attorney, Agent, or Firm*—Nixon and Vanderhye

[57] ABSTRACT

The invention relates to biochemically pure oligopeptides having stimulatory activity on osteoblastic and/or fibroblastic cells having a molecular weight between 200 and 2,000. Preferred oligopeptides according to the invention comprise the amino acid sequences Tyr-Gly-Phe-His-Gly (SEQ.ID.No.2) and Gly-Phe-Gly-Gly (SEQ.ID.No.3). The invention further relates to pharmaceutical compositions for the stimulation of formation of osteoblastic or fibroblastic cells, enhanced bone formation in osteogenic pathological conditions, fracture repair, healing of wounds, intraosseous implants and bone supplementation, or other conditions requiring enhanced bone formation cells comprising a therapeutically effective amount of an oligopeptide according to the invention.

20 Claims, 3 Drawing Sheets

OSTEOGENIC GROWTH OLIGOPEPTIDES AND PHARMACEUTICAL COMPOSITIONS CONTAINING THEM

FIELD OF THE INVENTION

The invention relates to osteogenic growth oligopeptides which possess stimulatory activity on osteoblastic and fibroblastic cells.

BACKGROUND OF THE INVENTION

It has been established that regenerating marrow induces an osteogenic response in distant skeletal sites and that this activity is mediated by factors released into the circulation by the healing tissue [Bab I. et al (1985) Calcif. Tissue Int. 37:551;Foldes, J. et al (1989) J. Bone Min. Res. 4:643;Einhorn, T. A. et al (1990) J. Bone Joint Surg. Am. 72:1374;Gazit D., et al (1990) Endocrinology 126:2607;Mueller, M. et al (1991) J. Bone Min. Res. 6:401]. One of these factors, a 14-amino acid osteogenic growth polypeptide (OGP), identical with the C-terminus of histone H4,has been recently identified [Bab, I. et al (1992) EMBO J. 11:1867;European Patent Applications Nos. 89201608.0and 90301862.0]. A histone H4fragment of the formula Tyr-Gly-Phe-Gly- Gly is disclosed in Kharchenko, E. P. et al (1989) Vopr. Med. Khim. 35( 2):106–9and in Kharchenko, E. P. et al (1987) Biull. Eksp. Biol. Med. 103(4):418–20.This peptide demonstrated analgesic and opiod activity.

Synthetic 14-mer osteogenic growth polypeptide (sOGP), identical in structure with the native molecule, has been shown to be a potent stimulator of proliferation of osteoblastic and fibroblastic cells in vitro. This synthetic polypeptide also stimulates osteoblastic cell alkaline phosphatase activity. When injected in vivo to rats, at very small doses, the synthetic osteogenic growth polypeptide increases bone formation and trabecular bone mass.

As in the case of other polypeptide growth regulators, such as growth hormone and insulin-like growth factor [Hintz, R. L. (1990) Horm. Res. 33:105], osteogenic growth polypeptide-binding protein/s (OGPBP) may protect the osteogenic growth polypeptide against proteolytic degradation [Bab, I. et al (1992) EMBO J. 11:18671.

C-terminal modified analogues of the osteogenic growth polypeptide, such as [$Cys^5$(NEM)]OGP-$NH_2$, bind to the OGPBP. The modified analogues do not share the OGP stimulation of cell proliferation and do not react with certain anti-OGP antibodies [Israel Patent Application No. 101747]. These polypeptide analogues can be used to release OGP from its complex with an OGPBP. If the competitive reaction takes place in a tissue culture medium, previously incubated with cells or a biological fluid having peptidase activity, the released OGP becomes exposed to protelolytic degradation resulting from said peptidase activity. Nevertheless, the possibility existed that short peptides resulting from the proteolytic degradation may retain the OGP activity.

Since the OGP molecule is too large for effective oral administration, it would be of therapeutic importance to find oligopeptides of six or less amino acids residues, that retain the OGP biological activity. such short oligopeptides could be modified into a stable pharmaceutical preparation suitable for oral or other systemic treatment of several pathological conditions, particularly conditions involving loss of bone tissue. In addition, the identification of such oligopeptides would be an essential step towards the definition of the minimal amino acid sequence that still retains the OGP activity, which may provide the basis for further drug design.

The present invention indeed relates to such native or synthetic osteogenically active oligopeptides.

The following abbreviations are used herein: OGP(s)-osteogenic growth polypeptide(s). OGPBP(s)-osteogenic growth polypeptide binding protein(s). irOGP-immunoreactive OGP. sOGP-synthetic OGP.

SUMMARY OF THE INVENTION

The invention relates to biochemically pure oligopeptides having stimulatory activity on osteoblastic and/or fibroblastic cells having a molecular weight between 200and 2,000.

Preferred oligopeptides according to the invention comprise the amino acid sequence: Tyr-Gly-Phe-His-Gly (SEQ ID NO:2) or the amino acid sequence Gly-Phe-Gly-Gly. (SEQ ID NO:3) Particularly preferred are oligopeptides wherein the five C-terminal amino acid residues are the five or four amino acid residues of said amino acid sequences.

The invention also relates to a method of isolating a biochemically pure oligopeptide having stimulatory activity on osteoblastic or fibroblastic cells from a biological sample comprising the steps of: (a) discarding from said biological sample peptides having a molecular weight lower than 3000;(b) incubating the medium obtained in step (a) with a polypeptide that binds to an osteogenic growth polypeptide binding protein/s and does not bind to an antibody directed against osteogenic growth polypeptide in the presence of protease inhibitors to compete said osteogenic growth polypeptide out from its complex with said osteogenic growth polypeptide binding protein/s; and (c) separating the immunoreactive osteogenic growth peptide from the reaction medium obtained in step (b) by chromatographic methods and to biochemically pure peptides having stimulatory activity on osteoblastic or fibroblastic cells prepared by this method.

In addition, the invention relates to pharmaceutical compositions for stimulating the formation of osteoblastic or fibroblastic cells, and consequent bond formation, comprising a therapeutically effective amount of an oligopeptide according to the invention and a pharmaceutically acceptable carrier.

BRIEF DESCRIPTION OF THE FIGURES

FIG. 1 shows production of steady-state and total irOGP by osteoblastic ROS 17/2.8(FIG. 1A) and MC3T3E1 osteoblastic cells (FIG. 1B) and NIH 3T3fibroblasts.(FIG. 1C) During the measurement period the cells were grown in chemically defined medium containing 4% BSA. Medium aliquotes for irOGP determination were obtained immediately after the addition of a BSA-containing medium ("0" time-point) and at the indicated times thereafter. Steady state and total irOGP were determined as before [Bab et al (1992) EMBO J. 11: 1867;Israel Patent Application No. 101747].

FIG. 4 shows the effect of OGP(10–14)(FIG. 4A) and OGP(10–14)His$^{13}$(FIG. 4B) (recovered from the respective B-1 and B-2 peaks of FIG. 3) on osteoblastic MC3T3E1 cell number in vitro. Dashed line-effect of positive SOGP control. Data are mean +SEM of triplicate cultures.

FIG. 5 shows the effect of synthetic OGP(10–14) (o--o-o--o--o) and OGP (10–14)His$^{13}$(▲-▲-▲) on osteoblastic MC3T3E1(FIG. 5A) and fibroblastic NIH 3T3(FIG. 5B) cell number in vitro. Cell cultures were set and challenged as in FIGS. 1 and 4. Cf. effect of positive sOGP control (□-□-□). Data are mean ±SEM of triplicate cultures presented as the ratio of treatment to BSA only control T/C ratio).

FIG. 6 shows the effect of synthetic Ac-Met$^0$OGP(10–14) on osteoblastic MC3T3E1(FIG. 6A) and fibroblastic NIH 3T3(FIG. 6B) cell number in vitro. Cell cultures were set and challenged as in FIGS. 1 and 4. Dashed line-effect of positive SOGP control. Data are mean ±SEM of triplicate cultures presented as the ratio of treatment to BSA only control (T/C ratio).

DETAILED DESCRIPTION OF THE INVENTION

OGP is a 14-residue polypeptide identified from regenerating bone marrow which has been shown to stimulate the proliferation and alkaline phosphatase activity of osteoblastic and fibroblastic cells in vitro and to increase bone formation and trabecular bone mass in rats when injected in vivo. The amino acid sequence of OGP is as follows:

Ala-Leu-Lys-Arg-Gln-Gly-Arg-Thr-Leu-Tyr-Gly-Phe-Gly-Gly (SEQ ID NO:4) Synthetic OGP, with an identical amino acid sequence and biological activity has been prepared by standard solid phase methodology. It has also been found that in different biological fluids OGP forms a complex with OGPBP(s) and that sOGP analogues modified at their C-terminal region can be used to competitively release the total irOGP from OGP- OGPBP complexes, as described above.

The inventors have found that if the competitive reaction takes place in a tissue culture medium, previously incubated with cells or a biological fluid having peptidase activity, the OGP released from the OGP-OGPBP complex becomes exposed to protelolytic degradation by said peptidase activity. Surprisingly, the inventors have found that short olgopeptides, which were found to be present in said competitive reaction medium, retain the stimulatory activity on osteoblastic and fibroblastic cells, and consequently on bone formation.

The invention thus relates to a biochemically pure oligopeptide having stimulatory activity on osteoblastic and/or fibroblastic cells having a molecular weight of 200 to 2,000, preferably 200 to 1,000.

Oligopeptides which can be specifically mentioned include those having 6 or more amino acids, preferably 6 to 10 amino acids. Other oligopeptides which can be specifically mentioned are those having 3 or 4 amino acids and those oligopeptides having 5 amino acids other than the pentamer Tyr-Gly-Phe-Gly-Gly.

Preferred oligopeptides according to the invention comprise the amino acid sequence: Tyr-Gly-Phe-His-Gly. Particularly preferred are oligopeptides wherein the five C-terminal amino acid residues are the five amino acid residues of said amino acid sequence. Most preferred is pentapeptide having the formula: Tyr-Gly-Phe-His-Gly. An additional preferred oligopeptide is the tetrapeptide Gly-Phe-Gly-Gly.

The invention also relates to a method of isolating a biochemically pure oligopeptide having stimulatory activity on osteoblastic or fibroblastic cells from a biological sample comprising the steps of: (a) discarding from said biological sample peptides having a molecular weight lower than 3000;(b) incubating the medium obtained in step (a) with a polypeptide that binds to an osteogenic growth polypeptide binding protein/s and does not bind to an antibody directed against osteogenic growth polypeptide in the presence of protease inhibitors to compete said osteogenic growth polypeptide out from its complex with said osteogenic growth polypeptide binding protein/s; and (c) separating the immunoreactive osteogenic growth peptide from the reaction medium obtained in step (b) by chromatographic methods.

The peptides having molecular weights lower than 3000 can be discarded by, for example ultra-filtration with a cut-off of 3000MW. The protease inhibitors can be commercially available inhibitors, for example E-64,Leupeptide or PMSF or mixtures thereof. The separation of the immunoreactive osteogenic growth peptide in step (c) can be accomplished by available HPLC techniques. A specific embodiment of the method of the invention is described in the Examples.

Biochemically pure peptides having stimulatory activity on osteoblastic or fibroblastic cells prepared by the method according to the invention are also within scope of the present invention. Preferred such peptides are biochemically pure peptides comprising the amino acid sequence: Tyr-Gly-Phe-Gly-Gly (SEQ ID NO:1) or the amino acid sequence: yr-Gly-Phe-His-Gly (SEQ ID NO:2).

Also within the scope of the invention is a hexapeptide having the formula Ac- et-Tyr-Gly-Phe-Gly-Gly and a tetrapeptide having the formula Gly-Phe-Gly-Gly.

As will be shown in the following Examples, the oligopeptides according to the invention, whether obtained by said method of isolation or synthesized, possess stimulatory activity on osteoblastic and fibroblastic cells, and may thus be of great therapeutical value. The invention therefore also relates to pharmaceutical compositions for stimulating the formation of osteoblastic or fibroblastic cells comprising a therapeutically effective amount of an oligopeptide having stimulatory activity on osteoblastic and/or fibroblastic cells having a molecular weight between 200 and 2000 and a pharmaceutically acceptable carrier.

Preferred pharmaceutical compositions according to the invention comprise a therapeutically effective amount of an oligopeptide comprising the amino acid sequence Tyr-Gly-Phe-His-Gly ( SEQ ID NO. 1), Tyr-Gly-Phe-Gly-Gly (SEQ ID NO. 2) or Gly-Phe-Gly-Gly (SEQ ID NO. 3) or a mixture thereof and a pharmaceutically acceptable carrier.

The pharmaceutical compositions of the invention may be particularly useful for the stimulation of osteoblastic cells and/or fibroblastic cells, and consequently enhanced bone formation in various pathological conditions, for example osteoporosis (or osteopenia of any etiology), fracture repair, healing of wounds, intraosseous implants and bone supplementation, or other conditions requiring enhanced bone formation.

The magnitude of a therapeutic dose of a polypeptide of the invention will of course vary with the group of patients (age, sex, etc.), the nature of the condition to be treated and with the particular polypeptide employed and its route of administration. In any case the therapeutic dose will be determined by the attending physician.

Any suitable route of administration may be employed for providing a mammal, especially a human, with an effective dosage of a polypeptide of this invention. Intravenous and oral administration may be preferred.

The pharmaceutical compositions of the invention can be prepared in dosage units forms. The dosage forms may also include sustained release devices. The compositions may be prepared by any of the methods well-known in the art of pharmacy.

The pharmaceutical compositions of the invention comprise as active ingredient an oligopeptide of this invention or a mixture of such oligopeptides in a pharmaceutically acceptable carrier, excipient or stabilizer, and optionally other therapeutic constituents. Acceptable carriers, excipients or stabilizers are non-toxic to recipients at the dosages and concentrations employed, and include buffers, such as phosphate buffered saline and like physiologically acceptable buffers, and more generally all suitable carriers, excipients and stabilizers known in the art.

EXAMPLES

Example 1- Purification and characterization of pentapeptides from tissue culture medium Materials Tissue culture ingredients were purchased from Biological Industries, Beit Haemek, Israel. Culture dishes were from Nunc, Roskilde, Denmark. bovine serum abumin (BSA), protease inhibitors and N-ethylmaleimide (NEM) were from Sigma Chemical Co., St. Louis, MO; Cat No. A-7030.Centricon-3microconentrators were purchased from Amicon, Inc. Beverly, MA. t-Boc-Gly $OCH_2$-Pam resin, N-Box protected amino acid derivatives, N,N-dicyclohexylcarbodiimide (DCC), 1-hydroxybenzotriazole (HOBt), diisopropylethylamine (DIEA), trifluoroacetic acid (TFA), N,N-dimethylformamide (DMF) and dichloromethane (CM) were obtained from Applied Biosystems Inc. (Foster City, Ca). Hydrogen fluoride (HF) was purchased from Mathesohn (Secacus, NJ), Boc-3- I-Tyr(BZ1)-OH from Bachem (Torrance Ca), p-Cresol from Aldrich Chemical Co. (Milwaukee, WI) and Sephadex G15F from Pharmacia (Uppsala, Sweden). C18reverse- phase column and acetonitrile were from E. Merck, Darmstadt, Germany. C4reverse- phase column was from The Separation Group, Hesparia CA.

Methods

Measuring irOGP accumulation in tissue culture media ROS 17/2.8or MC3T3E1 osteoblastic cells or NIH 3T3fibroblasts were maintained in α-Minimal Essential Medium supplemented with 10% fetal calf serum (FCS) and subcultured twice a week. Cells for experiments were derived from maintenance cultures at confluency. For the experiment the cells were seeded in $25cm^2$tissue culture flasks at 1x $10^4$cells/$cm^2$. The cultures were incubated at 37° C. in $CO_2$air. For the initial 46h the medium was supplemented with 10% FCS and 0.2% nucleosides/ribonucleosides followed by an additional 2h starvation period under serum free conditions. Then the serum free medium was replaced by 8ml medium containing 4% BSA. Half milliltre medium aliquots for irOGP determination were obtained immediately after the addition of BSA containing medium ("0" time-point) and 12, 24, 36and 48hrs thereafter. Steady state and total irOGP were determined in these aliquots as before [Bab et al. (1992) EMBO J. 11:1867;Israel Patent Application No. 101747].

Figure 2:
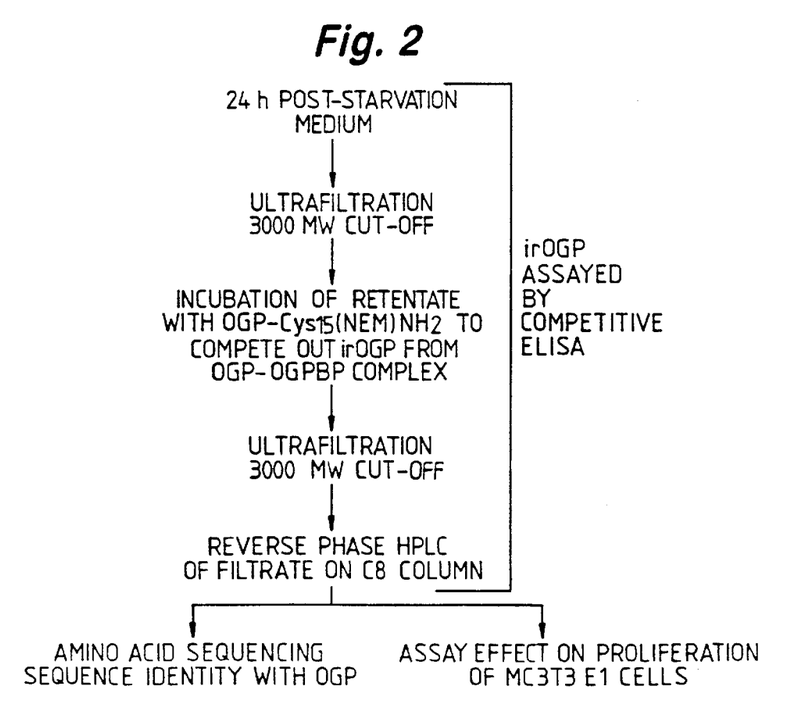
FIG. 2 is flow chart describing the purification of irOGP from 24h tissue culture medium prepared as described in FIG. 1 above using MC3T3E1 cells. Peptides of a molecular weight lower than 3000were separated by three repeated dilution/centrifugation cycles. The retentate was then incubated with [$Cys^{15}$(NEM)]OGP- $NH_2$, and recentrifuged. The filtrate was collected, and the irOGP separated from the [$Cys^{15}$(NEM)]OGP-$NH_2$using reverse phase HPLC and further purified as shown in FIG. 3. The purified irOGP in the peaks seen in FIG. 3 were subjected to amino acid sequencing by automated Edam's degradation and tested for proliferative activity as shown in FIG. 4.

Separation between irOGP and OGPBP FIG. 2 is a schematic demonstration of the separation between the irOGP and the OGPBP. A 3.75ml sample of medium collected 24h after cell starvation was diluted (1:1) with an equal amount phosphate buffered saline (PBS). The diluted medium was centrifuged in multiple centricon-3microconcentrators (Amicon, Inc., Beverly, MA) for 1.5h at 5,000x g. Polypeptides smaller than 3000MW were washed out of the retentate by three repeated dilution/centrifugation cycles using 1mM sodium azide in 165nM ammonium acetate pH 7.0as diluent. The minimal retentate volume allowed in each micro concentrator was 250μl. To release irOGP from the OGP-OGPBP complex, the 1:1diluted retentate was incubated for 30min at 37° C. with 450nmo/ml [$Cys^{15}$(NEM)]OGP- $NH_2$, prepared as before [Israel Patent Application No. 101747] in 165nM ammonium acetate containing 50μM E-64, 50μM Leupeptin and 500μM PMSF and recentrifuged.

Separation between irOGP and [$Cys^{15}$(NEM)]OGP-$NH_2$. The filtrate obtained by the microconcentration step was partially evaporated to final volume of 600μl. The irOGP content of the filtrate was 0.31nmol. The filtrate was divided into three equal aliquots. The irOGP in each of these aliquots was separated from the [$Cys^{15}$(NEM)]OGP-$NH_2$by HPLC using a reverse phase Vydac protein C4column employing the following acetonitrile gradient run at a flow rate of 1ml/min: 3ml 12% acetonitrile; and 30ml 12-19% acetonitrile.

Separation between two irOGP peaks Half ml fractions comprising the main irOGP peak recovered from the C4column were pooled and partially evaporated to final volume of 400μl. The irOGP content of this peak was 0.26nmol. The filtrate was divided into two equal aliquots. The irOGP in each of these aliquots was subjected to HPLC on a reverse-phase C18column employing the following acetonitrile gradient run at a flow rate of 1/ml/min: 3ml 14% acetonitrile and 30ml 14-19% acetonitrile.

Amino acid sequence determination Protein in the two irOGP peaks recovered from the C18column was subjected to automated peptide sequence analysis in an Applied Biosystems 470A sequencer using the program and reagents supplied by the manufacturer. Released amino acid derivatives were identified with the aid of an on-line HPLC system.

Figure 1A:
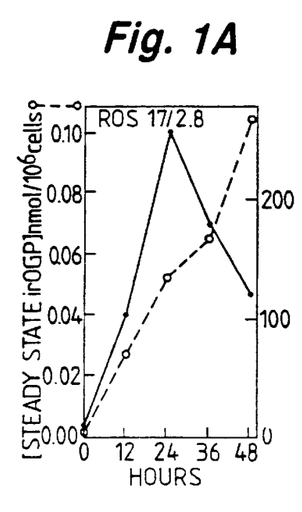
Figure 1B:
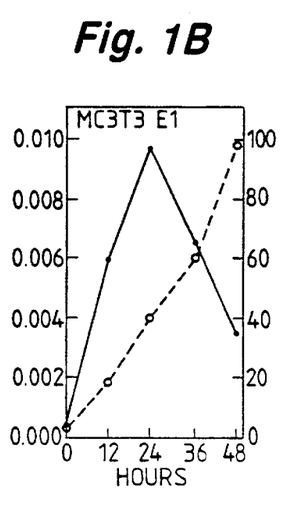
Figure 1C:
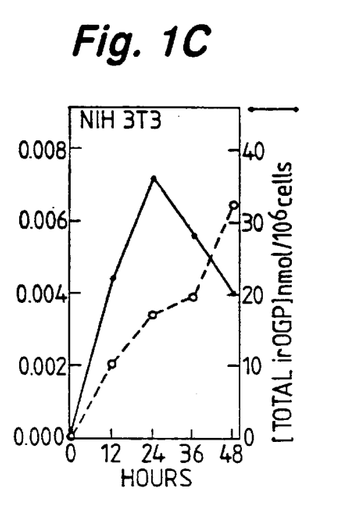

Results FIG. 1 shows that in all three cell systems studies, the total irOGP reached a peak 24h after starvation and exposure to the chemically defined medium. This time period coincides with the confluency of the cultures. During the next 24h there was an approximately 50% decrease in the total irOGP. The steady state irOGP showed a more or less linear increase during the whole detection period. These results indicate that stromal cells produce irOGP and the OGPBP. The rate of synthesis of the irOGP and/or the OGPBP decreases when the cultures reach confluency.

The 24h culture medium from the MCT3E1 cells was subjected to repeated dilution/centrifugation cycles to remove the non-bound irOGP and other peptides with molecular weight smaller than 3000(FIG. 2). Only 0.96% of the total irOGP could be discarded in this way. The remaining irOGP was left in the form of OGP-OGPBP complex that was contained in the retentate because of its high molecular weight. (Table A). The HPLC separation of [$Cys^{15}$(NEM)]OGP-$NH_2$resulted in three major light absorption peaks. The greater of these peaks eluted at 19.5–23.5min retention time, a position similar to that of [$Cys^{15}$(NEM)]OGP-$NH_2$run separately under the same conditions. This peak did not show OGP immunoreactivity. Both other peaks were only partially separated from each other and showed a high irOGP content (FIG. 1A), 11.5% that of the total irOGP present in the culture medium (Table A). It is likely that most of this decrease in irOGP content resulted from peptidase activity during the displacement reaction, in spite of the presence of peptidase inhibitors. To enhance the separation between these irOGP peaks the respective fractions (retention time 11–12.5min) were pooled and subjected to a second HPLC step that resulted in two distinct light absorption peaks, both showing high irOGP conent (FIG. 1B). These peaks were designated B-1 and B-2.

TABLE A

RECOVERY OF IMMUNOREACTIVE OGP FROM INDIVIDUAL PURIFICATION STEPS

| Purification step | irOGP (total nmol in preparation) | percent recovery |
|---|---|---|
| 24-h post starvation medium | 270.0 | 100 |
| Initial ultrafiltration | 2.6 | 0.96 |
| Post-displacement ultrafiltration | 31.0 | 11.5 |
| Reverse-phase HPLC | 12.6 | 4.7 |

The respective fractions eluted with retention times 23.5–24min and 25–25.5min were pooled. Aliquots of the pooled fractions were allocated for testing their proliferative effect in the MC3T3E1 cell assay. Amino acid sequencing revealed that peak B-1contained a pentapeptide identical to the C-terminal region (residues 10–14) of OGP. Peak B-2contained a similar pentapeptide in which $Gly^{13}$ of the OGP was substituted by His (Table B)

TABLE B

AMINO ACID SEQUENCES OF PENTAPEPTIDES

| | | |
|---|---|---|
| Peak B-1* | Tyr—Gly—Phe—Gly—Gly | (SEQ ID NO: 1) |
| Peak B-2* | Tyr—Gly—Phe—His—Gly | (SEQ ID NO: 2) |

Figure 3A:
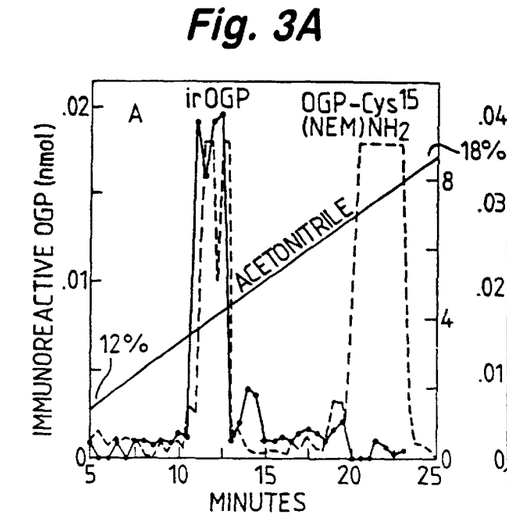
(FIG. 3A) and B-the two irOGP peaks, using Merck C18 reverse-phase column. Dashed and continuous lines represent light absorbance and immunoreactivity, respectively.
Figure 3B:
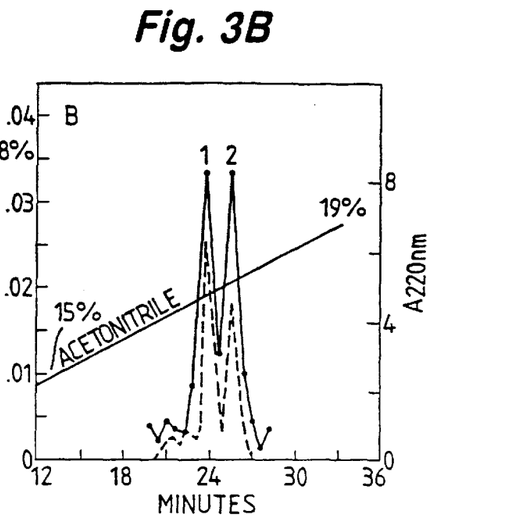
FIG. 3 shows HPLC separation of A-irOGP and [$Cys^{15}$(NEM)]OGP-$NH^2$using reverse phase Vydac C4column.

*Defined in FIG. 3.

Figure 4A:
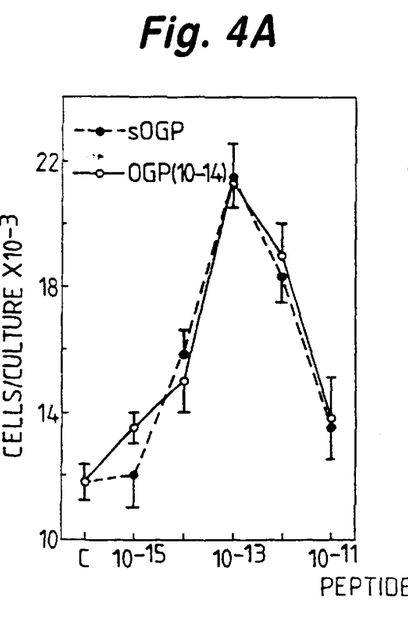
Figure 4B:
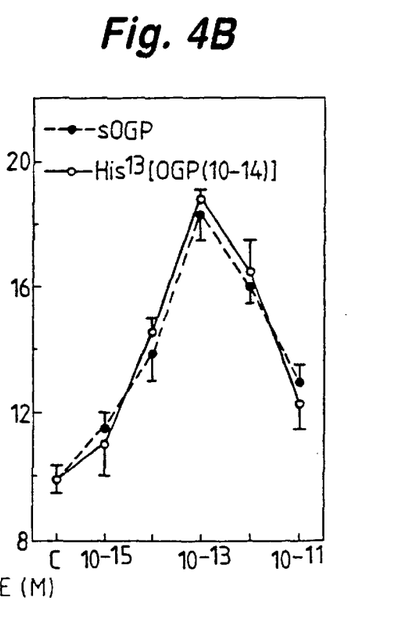

The proliferative activity of either peak in the MC3T3E1 cell assay was identical to that of positive sOGP controls with a peak at $10^{13}$M (FIG. 4).

Example 2- Activity of Synthetic Pentapeptides

Peptide synthesis Synthetic peptides of this invention were prepared by solid phase method of Merrifield [Merrifield, (1969) Adv. Enzymol. 32: 221] using an Applied biosystems Model.430A Automated peptide Synthesizer (Applied Biosystems Inc., Foster City, CA). In the case of peptide free acid the synthesis was carried out on 0.5 mmol t-Boc-Gly-PAM resin (1% cross-linked, 0.61meq/g). t-Boc- Gly-MBHA resin (1% cross-linked, 0.66 meq/g) was used for the amidated tetrapeptide. The amino acid derivatives were protected on the αamino function by t-butyloxycarbonyl (Boc) groups. Protection of the tyrosine side chain was by Z. The amino acid derivatives were coupled via the DCC-mediated preformed symmetrical anhydride method of Hagemaier, H. and Frank, H. [Hoppe-Seyler's Z. (1972) Physiol. Chem. 353:1973]. The coupling of each amino acid residue was repeated twice. Deprotection of the blocked amino terminus was by treatment with 25% TFA in DCM. Side chains were deprotected and the peptide cleaved from the resin using the HF procedure where a mixture of 4ml anisole and 36ml liquid HF was used for 75min at 0° C. The crude synthetic peptides were purified on a Merck-Hitachi 655A-11HPLC instrument equipped with a Waters μBondPark™ C18column (1.9× 15.0cm). The cartridge was pumped with acetonitrile linear gradients containing TFA (Table C) at a flow rate of 6.0ml/min.

The BH-OGP (11–14) (BH =Bolton-Hunter) was prepared by reacting 3(3-iodo4-hydroxyphenyl) propionic acid N-hydroxysuccinimidyl ester with purified OGP (11–14) using the method of Michelot et al [Michelot R. et al (1980) Biochem. Biophys. Res. Comm. 95:491–498].

TABLE C

ACETONITRILE LINEAR GRADIENTS USED FOR HPLC PURIFICATION OF DI-, TRI-, TETRA-, PENTA- AND HEXA-OGP RELATED PEPTIDES

| | Gradient | | |
|---|---|---|---|
| Peptide | (% Acetonitrile) | Time (min) | % TFA |
| OGP (13–14) | 0% isocratic | 30 | .1 |
| OGP (11–12) | 0% isocratic | 30 | .1 |
| OGP (12–14) | 0% isocratic | 30 | .1 |
| OGP (11–13) | 0% isocratic | 30 | .1 |
| OGP (10–12) | 0–25 | 120 | .1 |
| OGP (11–14) | 0–30 | 120 | .1 |
| BH*-OGP(11–14) | 0–25 | 90 | .1 |
| OGP(11–14)NH$_2$ | 0–5 | 90 | .05 |
| OGP(10–13) | 0–25 | 120 | .1 |
| OGP(10–14) | 0–20 | 100 | .1 |
| OGP(10–14)His$^{13}$ | 0–20 | 100 | .1 |
| Ac—Met$^0$[OGP(10–14)] | 0–20 | 150 | .1 |

*BH = Bolton-Hunter reagent

Table D demonstrates the conversion between the nomenclature used herein and amino acid sequence of the peptides.

TABLE D

AMINO ACID COMPOSITION OF SYNTHETIC DI-, TRI-, TETRA-, PENTA- AND HEXA- OGP RELATED PEPTIDES

| | |
|---|---|
| OGP (13-14) | Gly—Gly |
| OGP (11-12) | Gly—Phe |
| OGP (12-14) | Phe—Gly—Gly |
| OGP (11-13) | Gly—Phe—Gly |
| OGP (10-12) | Tyr—Gly—Phe |
| OGP (11-14) | Gly—Phe—Gly—Gly (SEQ ID NO: 3) |
| BH*-OGP(11-14) |  |
| OGP (11-14) NH$_2$ | Gly—Phe—Gly—Gly—NH2 (SEQ ID NO: 3) |
| OGP (10-13) | Tyr—Gly—Phe—Gly (SEQ ID NO: 7) |
| OGP (10-14) | Tyr—Gly—Phe—Gly—Gly (SEQ ID NO: 1) |
| OGP (10-14) His | Tyr—Gly—Phe—His—Gly (SEQ ID NO: 2) |
| Ac-Met$^0$[OGP(10-14)] | Ac—Met—Tyr—Gly—Phe—Gly—Gly (SEQ ID NO: 5) |

*BH = Bolton-Hunter reagent

Results

Figure 5A:
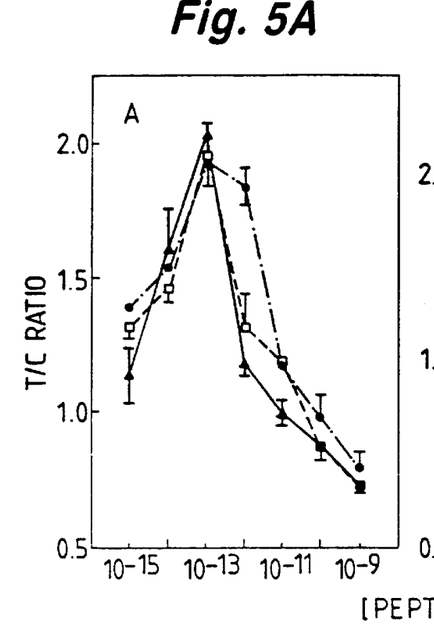
Figure 5B:
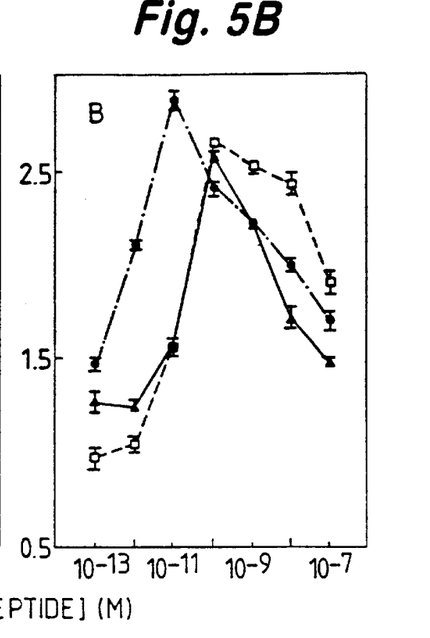

The proliferative effect of either pentapeptide in the MC 3T3E1 and NIH 3T3cell assays was similar to that of sOGP positive controls. The respective peak activities were at $10^{-13}$ and $10^{-11-10-10}$M peptide concentration (FIG. 5).

Example 3-Proliferative effect of hexapeptide

The hexapeptide of Ac-Met⁰[OGP(10–14)] was prepared for testing the feasibility of using Ac-[$^{35}$S MET OGP (10–14)] for metabolic and binding studies.

Results

Figure 6A:
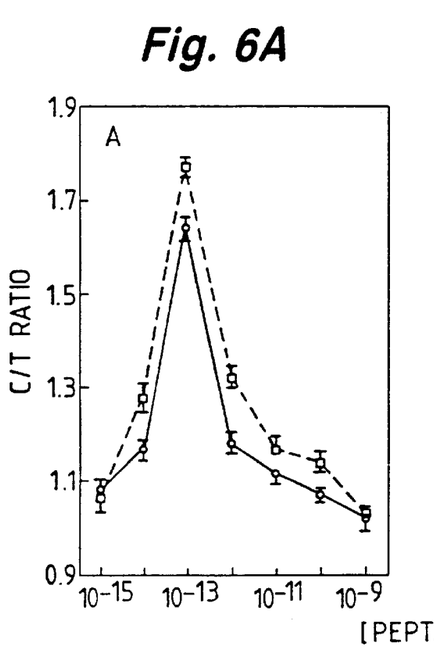
Figure 6B:
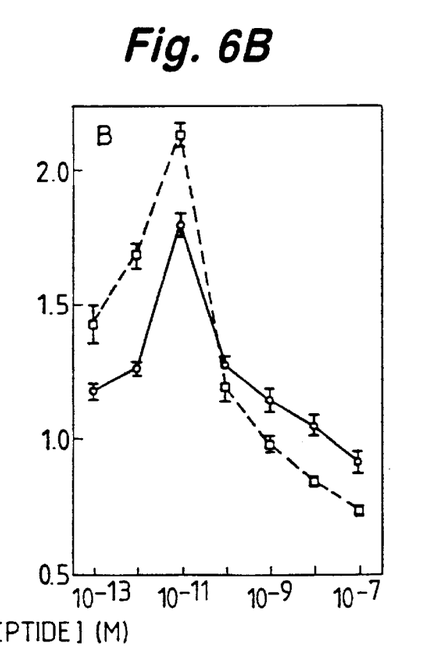

The Ac-Met⁰[OGP](10–14)] stimulated the MC 3T3E1 and NIH 3T3cell number in a manner closely similar to that of positive sOGP controls with peaks at $10^{-13}$ and $10^{-11}$M peptide concentration, respectively (FIG. 6).

Example 4-Proliferative effect of tetra-, tri-and di-peptides

All the five tetrapeptides had a dose-response effect on the MC 3T3E1 and NIH 3T3cell number With peaks at $10^{-13}$ and $10^{-11}$M peptide concentration, respectively. The magnitude of the BH-OGP (11–14), peak effect in either cell system was highest and similar to that of the SOGP positive control.

The peak activity of the OGP(11–14), OGP(10–13) and OGP (10–12) showed intermediate values. The OGP (11–14) NH₂showed the lowest peak effect. OGP (12–14), OGP (11–13), OGP(13–14) and OGP (11–12) did not affect the MC 3T3E1and NIH 3T3cell number (Table E).

TABLE E

PROLIFERATIVE ACTIVITY OF SYNTHETIC
DI-, TRI- AND TETRA-OGP RELATED PEPTIDES
{Percent Activity of Full Length Peptide [OGP(1–14)]}

| Peptide | MC3T3 E1 | | | NIH 3T3 | | |
|---|---|---|---|---|---|---|
| | Mean | Range | No. of Expers. | Mean | Range | No. of Expers |
| BH*-OGP(11–14) | 113 | 70–137 | 3 | 80 | 63–112 | 3 |
| OGP(11–14) | 66 | 34–100 | 8 | 68 | 34–100 | 4 |
| OGP(10–13) | 58 | 42–74 | 2 | 89 | 89 | 1 |
| OGP(10–12) | 41 | 41 | 1 | 57 | 57 | 1 |
| OGP(11–14)NH₂ | 25 | 19–31 | 2 | 33 | 31–35 | 2 |
| OGP(12–14) | 0 | 0 | 3 | 0 | 0 | 3 |
| OGP(11–13) | 0 | 0 | 3 | 0 | 0 | 3 |
| OGP(13–14) | 0 | 0 | 3 | 0 | 0 | 3 |
| OGP(11–12) | 0 | 0 | 3 | 0 | 0 | 3 |

*BH—Bolton-Hunter reagent.

We claim:

1. An oligopeptide having stimulatory activity on osteoblastic and/or fibroblastic cells, said oligopeptide having a molecular weight of from 200 to 1,000 and comprising the amino acid sequence: Tyr-Gly-Phe-His-Gly (SEQ ID NO:2).

2. An oligopeptide according to claim 1 wherein the five C-terminal amino acid residues are: Tyr-Gly-Phe-His-Gly (SEQ ID NO:2).

3. A pentapeptide having the formula: Tyr-Gly-Phe-His-Gly (SEQ ID NO:2).

4. An oligopeptide having the formula: Ac-Met-Tyr-Gly-Phe-Gly-Gly (SEQ ID NO:5).

5. A method of isolating an oligopeptide having stimulatory activity on osteoblastic or fibroblastic cells, said oligopeptide having a molecular weight of from 200 to 1,000, from a biological sample which is an osteoblast or fibroblast culture medium, said method comprising the steps of:

(a) discarding from said biological sample peptides having a molecular weight lower than 3000;

(b) incubating the medium obtained in step (a) with (Cys$^{15}$(NEM))oGP-nH$_2$; and (c) separating osteogenic growth peptides from the reaction medium obtained in step (b) by chromatographic methods.

6. A method according to claim 5 wherein, in step (a), the peptides having molecular weights lower than 3000 are discarded by ultra-filtration with a cut-off of 3000 MW.

7. A method according to claim 5 wherein said protease inhibitors are E-64, Leupeptin or PMSF or mixtures thereof.

8. A method according to claim 5 wherein in step (c) the osteogenic growth peptide is separated by HPLC.

9. An oligopeptide obtained by the method of claim 5 and comprising the amino acid sequence: Tyr-Gly-Phe-His-Gly$_2$,(SEQ ID NO:2).

10. A pharmaceutical composition comprising an oligopeptide having stimulatory activity on osteoblastic and/or fibroblastic cells, said oligopeptide having a molecular weight of from 200 to 1,000 and comprising the amino acid sequence: Tyr-Gly-Phe-His-Gly(SEQ ID NO:2); and a pharmaceutically acceptable carrier.

11. A pharmaceutical composition according to claim 10 wherein the five C-terminal amino acid residues are: Tyr-Gly-Phe-His-Gly (SEQ ID NO:2),and a pharmaceutically acceptable carrier.

12. A pharmaceutical composition comprising a pentapeptide having the formula: Tyr-Gly-Phe-His-Gly(SEQ ID NO:5); and a pharmaceutically acceptable carrier.

13. A pharmaceutical composition comprising an oligopeptide having the formula: Ac-Met-Tyr-Gly-Phe-Gly-Gly(SEQ ID NO:3); and a pharmaceutically acceptable carrier.

14. A pharmaceutical composition comprising a tetrapeptide having the formula Gly-Phe-Gly-Gly(SEQ ID NO:3); and a pharmaceutically acceptable carrier.

15. A method of treatment of a human or animal patient to effect stimulation of formation of osteoblastic or fibroblastic cells, enhanced bone formation in osteopenic pathological conditions, fracture repair, healing of wounds, intraosseous implants and bone supplementation, and other conditions requiring enhanced bone formation cells which comprises administering to the human or animal patient a therapeutically effective amount of an oligopeptide according to claim 1.

16. A method according to claim 15 wherein the oligopeptide is an oligopeptide of claim 3.

17. A method according to claim 15 wherein the oligopeptide is an oligopeptide of claim 3.

18. A method of treatment of a human or animal patient to effect stimulation of formation of osteoblastic or fibroblastic cells, enhanced bone formation in osteopenic pathological conditions, fracture repair, healing of wounds, intraosseous implants and bone supplementation, and other conditions requiring enhanced bone formation cells which comprises administering to the human or animal patient a therapeutically effective amount of an oligopeptide having the formula: Ac-Met-Tyr-Gly-Phe-Gly-Gly(SEQ ID NO:5).

19. A method of treatment of a human or animal patient to effect stimulation of formation of osteoblastic or fibroblastic cells, enhanced bone formation in osteopenic pathological conditions, fracture repair, healing of wounds, intraosseous implants and bone supplementation, and other conditions requiring enhanced bone formation cells which comprises administering to the human or animal patient a therapeutically effective amount of a tetrapeptide having the formula Gly-Phe-Gly-Gly(SEQ ID NO:3).

20. A method of treatment of a human or animal patient to effect stimulation of formation of osteoblastic or fibroblastic cells, enhanced bone formation in osteopenic pathological conditions, fracture repair, healing of wounds, intraosseous implants and bone supplementation, and other conditions requiring enhanced bone formation cells which comprises administering to the human or animal patient a therapeutically effective amount of a pentapeptide having the formula: Tyr-Gly-Phe-Gly-Gly(SEQ ID NO:1).

* * * * *

UNITED STATES PATENT AND TRADEMARK OFFICE
CERTIFICATE OF CORRECTION

PATENT NO. : 5,814,610
DATED : September 29, 1998
INVENTOR(S) : Bab et al

It is certified that error appears in the above-identified patent and that said Letters Patent is hereby corrected as shown below:

Column 3, line 9, delete "+" insert -- ± --.

Column 4, line 30, delete "yr" insert --Tyr--.

Column 4, line 32, delete "Ac-et" insert --Ac-Met--.

Column 4, line 48, delete "NO:1" insert --NO:2--.

Column 4, line 49, delete "NO. 2" and insert -- NO:1--.

Column 9, line 9, delete "$10^{-11-10-10}$" and insert --$10^{-11}-10^{-10}$--.

Column 13, line 48, delete "oGP-hH$_2$" and insert --OGP-NH$_2$--.

Column 14, line 34, delete "NO:5" and insert --NO:2"

Column 14, line 37, delete "NO:3" and insert -- NO:5--.

Signed and Sealed this

Third Day of August, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO: 1:

Tyr  Gly  Phe  Gly  Gly
    1                                5

( 2 ) INFORMATION FOR SEQ ID NO: 2:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO: 2:

```
        Tyr  Gly  Phe  His  Gly
        1                   5
```

(2) INFORMATION FOR SEQ ID NO: 3:

(i) SEQUENCE CHARACTERISTICS:
        (A) LENGTH: 4 amino acids
        (B) TYPE: amino acid
        (D) TOPOLOGY: linear     (ii) MOLECULE TYPE: peptide     (xi) SEQUENCE DESCRIPTION: SEQ ID NO: 3:

```
        Gly  Phe  Gly  Gly
        1
```

(2) INFORMATION FOR SEQ ID NO: 4:

(i) SEQUENCE CHARACTERISTICS:
        (A) LENGTH: 14 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 14
        (D) OTHER INFORMATION: /note= "This peptide (OGP) may
            additionally comprise a 15th amino acid, namely
            CYS, at the C-terminus. This modified peptide is
            known as [Cys15(NEM)]OGP-NH2."

(xi) SEQUENCE DESCRIPTION: SEQ ID NO: 4:

```
        Ala  Leu  Lys  Arg  Gln  Gly  Arg  Thr  Leu  Tyr  Gly  Phe  Gly  Gly
        1              5                             10
```

(2) INFORMATION FOR SEQ ID NO: 5:

(i) SEQUENCE CHARACTERISTICS:
        (A) LENGTH: 4 amino acids
        (B) TYPE: amino acid
        (D) TOPOLOGY: linear     (ii) MOLECULE TYPE: peptide     (ix) FEATURE:
        (A) NAME/KEY: Modified-site
        (B) LOCATION: 1
        (D) OTHER INFORMATION: /note= "This peptide's N-terminus may
            be attached to a Bolton-Hunter reagent, whose formula
            is given in the description at, for example, Page 13,
            Table D. The modified peptide is known as
            BH*-OGP(11- 14)."

(ix) FEATURE:
        (A) NAME/KEY: Modified-site
        (B) LOCATION: 4
        (D) OTHER INFORMATION: /note= "An NH2 group may be
            attached to the C-terminus of this peptide.The
            modified peptide is known as OGP(11-14)-NH2."

(xi) SEQUENCE DESCRIPTION: SEQ ID NO: 5:

```
        Gly  Phe  Gly  Gly
        1
```

(2) INFORMATION FOR SEQ ID NO: 6:

(i) SEQUENCE CHARACTERISTICS:
        (A) LENGTH: 6 amino acids
        (B) TYPE: amino acid
        (D) TOPOLOGY: linear -continued

```
( i i ) MOLECULE TYPE: peptide ( i x ) FEATURE:
        ( A ) NAME/KEY: Modified-site
        ( B ) LOCATION: 1
        ( D ) OTHER INFORMATION: /note= "This peptide is attached,
              at its C- terminus, to an Ac group. The peptide is
              known as Ac- MetO[OGP(10-14)]."

( x i ) SEQUENCE DESCRIPTION: SEQ ID NO: 6:

Met   Tyr   Gly   Phe   Gly   Gly
    1                       5

( 2 ) INFORMATION FOR SEQ ID NO: 7:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO: 7:

Tyr   Gly   Phe   Gly
    1
```